(12) United States Patent
Onishi et al.

(10) Patent No.: US 6,906,224 B2
(45) Date of Patent: Jun. 14, 2005

(54) PROCESS FOR PRODUCING α-AMINOKETONES

(75) Inventors: Tomoyuki Onishi, Kawasaki (JP);
Naoko Hirose, Kawasaki (JP);
Takayuki Suzuki, Kawasaki (JP);
Takashi Nakano, Kawasaki (JP);
Masakazu Nakazawa, Kawasaki (JP);
Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/695,809

(22) Filed: Oct. 30, 2003

(65) Prior Publication Data

US 2004/0210089 A1 Oct. 21, 2004

Related U.S. Application Data

(62) Division of application No. 10/290,266, filed on Nov. 8, 2002, now Pat. No. 6,696,571, which is a division of application No. 09/943,361, filed on Aug. 31, 2001, now Pat. No. 6,570,039, which is a continuation of application No. PCT/JP00/01336, filed on Mar. 6, 2000.

(30) Foreign Application Priority Data

Mar. 5, 1999 (JP) ............................................. 11-59446

(51) Int. Cl.[7] ...................... C07C 209/62; C07D 301/28
(52) U.S. Cl. ...................... 564/487; 564/496; 549/513; 549/514
(58) Field of Search ................................ 564/487, 496; 549/513, 514

(56) References Cited

U.S. PATENT DOCUMENTS 5,559,256 A 9/1996 Gordon et al.
6,500,985 B2 12/2002 Onishi et al.
6,538,160 B2 3/2003 Onishi et al.
6,639,094 B2 10/2003 Onishi et al.
6,683,214 B2 1/2004 Onishi et al.

FOREIGN PATENT DOCUMENTS

WO 97/19681 6/1997

OTHER PUBLICATIONS

Richard W. Draper, et al., "Novel Steroselective Synthesis of the Fused Benzazepine Dopamine $D_1$ Antagonist (6aS, 13bR)–11–Chloro–6, 6a, 7, 8, 9, 13b–Hexahydro–7–Methyl–5H–Benzo[d]Naphth[2,1–b] Azepin–12–ol (SCH 39166):2,L–Homophenylalanine––Based Syntheses", Organic Process Research & Development, vol. 2, No. 3, (1998), pp. 186–192.

Magnus W. Walter, et al., "Reaction of (Trifluoromethyl) Trimethylsilane with Oxazolidin–5–Ones: Synthesis of Peptidic and Nonpeptidic Trifluoromethyl Ketones", J. Organic Chemistry, (1998), 63, pp. 5179–5192.

Magnus W. Walter, et al., "Reaction of Ruppert's Reagent (TMS–CF3) with Oxazolidinones: Synthesis of Protected Alpha–Amino Trifluoromethylketones", Tetrahedron Letters, vol. 36, No. 42, pp. 7761–7764 (1995).

Primary Examiner—Brian Davis
(74) Attorney, Agent, or Firm—Oblon, Spivak, McClelland, Maier & Neustadt, P.C.

(57) ABSTRACT

A process for producing α-aminohalomethyl ketones or N-protected α-aminohalomethyl ketones from specified 3-oxazolidin-5-one derivatives via 5-halomethyl-5-hydroxy-3-oxazolidine derivatives. By this process, α-aminohalomethyl ketones and compounds relating to them can be obtained efficiently and economically in industrial scale.

7 Claims, No Drawings

PROCESS FOR PRODUCING α-AMINOKETONES

CROSS-REFERENCE TO RELATED APPLICATIONS

The present application is a Divisional application of U.S. Ser. No. 10/290,266 filed on Nov. 8, 2002 now U.S. Pat. No. 6,696,571, which is a Divisional application of U.S. Ser. No. 09/943,361 filed on Aug. 31, 2001, now U.S. Pat. No. 6,570,039, which is a Continuation application of PCT/JP00/01336 filed on Mar. 6. 2000.

BACKGROUND OF THE INVENTION

The present invention relates to a process for producing α-aminohalomethyl ketones or N-protected α-aminohalomethyl ketones from specified 3-oxazolidin-5-one derivatives via 5-halomethyl-5-hydroxy-3-oxazolidine derivatives.

The present invention also relates to a process for producing β-aminoalcohols, N-protected β-aminoalcohols or N-protected β-aminoepoxides from the α-aminohalomethyl ketones or N-protected α-aminohalomethyl ketones.

The α-aminohalomethyl ketones and salts thereof can be converted into peptidylhalomethyl ketones by a method usually employed in peptide synthesis. These α-aminohalomethyl ketones and salts thereof are useful as intermediates for synthesizing various peptidylhalomethyl ketones known as serine protease inhibitors (see, for example, W. Brandt et al., Int. J. Peptide Protein Res. 46, 1995, 73).

It was reported that the α-aminohalomethyl ketones and salts thereof are also useful as intermediates for synthesizing HIV protease inhibitors (see, for example, J. Med. Chem. 1990, 33, 1285).

It is also known that N-protected α-aminohalomethyl ketones, β-aminoalcohols as well as N-protected β-aminoalcohols and N-protected β-aminoepoxides derived from them are also known to be important intermediates for HIV protease inhibitors. α-Aminohalomethyl ketones were produced by removing a protecting group from N-protected α-aminohalomethyl ketones (see, for example, S. Fittkau et al., J. Prakt. Chem. 1986, 529).

For the production of N-protected α-aminohalomethyl ketones, for example, there is known a process wherein an amino acid ester in which the amino group is protected is reacted with a metal enolate obtained from an α-haloacetic acid and a resulting product is followed by decarboxylation (WO 96/23756).

However, in this process, about 4 equivalents or more of an expensive Grignard reagent or organic lithium reagent is necessitated for 1 equivalent of the N-protected amino acid ester as shown in Examples in WO 96/23756.

Further, a process wherein an alanine ester in which the amino group is protected with dibenzyl group is reacted with a halomethyllithium is known (see J. Barluenga et al., J. Chem. Soc., Chem. Commun. 1994, 969).

However, only dibenzyl group is discussed as the protective group for the amino group in this process, and no other protective group is described therein. In addition, because no process is known for removing the protecting group from the dibenzyl group while the halogenated ketone group is kept, the process of J. Barluenga et al. cannot be employed for the production of α-aminohalomethyl ketones.

There is also known another process wherein a carbamato part of an amino acid ester in which the amino group is protected with the carbamato group is further protected with a trialkylsilyl group and then this compound is reacted with a halomethyllithium (J. P. KOKAI Nos. Hei 8-99947 and Hei 8-99959).

However, also in this process, about 2.2 equivalents of an expensive organic lithium reagent is necessitated for 1 equivalent of the N-protected amino acid ester as described in Examples in J. P. KOKAI Nos. Hei 8-99947 and Hei 8-99959. Although the protecting group for the amino group used in these Examples is only methoxycarbonyl group, no process for removing the methoxycarbonyl group while keeping the halogenated ketone group is known yet. It is not yet proved that this process can be employed for the production of α-aminohalomethyl ketones.

DISCLOSURE OF THE INVENTION

The object of the present invention is to provide an economical, efficient process for producing α-aminohalomethyl ketones and related compounds on an industrial scale.

After intensive investigations made for the purpose of solving the above-described problems, the inventors have found that α-aminohalomethyl ketones or N-protected α-aminohalomethyl ketones can be obtained in a high yield by reacting a 3-oxazolidin-5-one derivative with a halomethyllithium to form a 5-halomethyl-5-hydroxy-3-oxazolidine derivative and treating this derivative with an acid.

Namely, the present invention provides a process for producing N-protected α-aminohalomethyl ketones of following general formula (3):

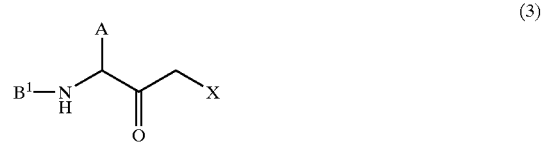

(3)

wherein A represents an unsubstituted or substituted alkyl group having 1 to 10 carbon atoms, aryl group having 6 to 15 carbon atoms or aurally group having 7 to 20 carbon atoms, or a group corressponding thereto which contains a hetero atom in the carbon skeleton; $B^1$ represents a protecting group for the amino group; and X represents a halogen atom, α-aminohalomethyl ketones of following general formula (4):

(4)

wherein A and X are as defined above, or salts thereof, which comprises the steps of reacting a 3-oxazolidin-5-one derivative of following general formula (1):

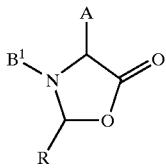
(1)

wherein R represents an unsubstituted or substituted aryl group or lower alkyl group or hydrogen atom, and A and $B^1$ are as defined above with a halomethyllithium and then treating the reaction product with an acid.

The present invention also provides 5-halomethyl-5-hydroxy-3-oxazolidine derivatives of following general formula (2):

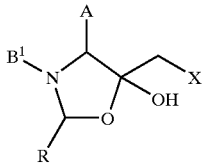
(2)

wherein R represents an unsubstituted or substituted aryl group or lower alkyl group or hydrogen atom, A represents an unsubstituted or substituted alkyl group having 1 to 10 carbon atoms, aryl group having 6 to 15 carbon atoms or aralkyl group having 7 to 20 carbon atoms, or a group corresponding thereto which contains a hetero atom in the carbon skeleton; $B^1$ represents a protecting group for the amino group; and X represents a halogen atom.

The present invention further provides 3-oxazolidin-5-one derivatives of following general formula (16)

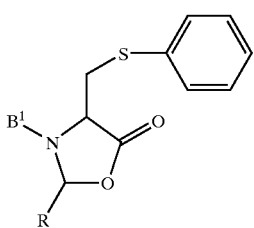
(16)

wherein R represents an unsubstituted or substituted aryl group or lower alkyl group or hydrogen atom, and $B^1$ represents a protecting group for the amino group.

BEST MODE FOR CARRYING OUT THE INVENTION

In the formulae in the present invention, R represents an unsubstituted or substituted aryl group or lower alkyl group or hydrogen atom. When those groups have a substituent, the substituent is an alkoxyl group, nitro group, an alkyl group, a halogen atom or the like. The aryl group is preferably phenyl group which may have a substituent. The lower alkyl groups are preferably straight or branched, saturated alkyl groups having 1 to 4 carbon atoms.

A in the formulae in the present invention represents hydrogen atom, an unsubstituted or substituted alkyl group having 1 to 10 carbon atoms, aryl group having 6 to 15 carbon atoms or aralkyl group having 7 to 20 carbon atoms, or a group corresponding thereto which contains a hetero atom in the carbon skeleton. When those groups have a substituent, the substituent is an alkoxyl group, nitro group, an alkyl group, a halogen atom or the like.

Such a group can be introduced into the compound from, e.g., an amino acid. For example, when A is hydrogen atom, it can be introduced by using glycine as the starting material. In the same way, methyl group can be introduced by using alanine; isopropyl group can be introduced by using valine; 2-methylpropyl group can be introduced by using leucine; 1-methylpropyl group can be introduced by using isoleucine; benzyl group can be introduced by using phenylalanine; and methylthioethyl group can be introduced by using methionine.

A may be a group introduced by using an amino acid in which a functional group in a side chain thereof is protected, such as S-t-butylcysteine, S-tritylcysteine, S-(p-methylbenzyl)cysteine, S-(p-methoxybenzyl)cysteine, O-t-butylserine, O-benzylserine, O-t-butylthreonine, O-benzylthreonine, O-t-butyltyrosine or O-benzyltyrosine, as the starting material.

A is not limited to a group introduced from a starting material derived from a natural amino acid, but it may a group introduced from a starting material derived from a synthetic amino acid (such as phenylthiomethyl group). A is preferably benzyl group or phenylthiomethyl group.

X in the formulae in the present invention represents a halogen atom. The halogen atoms include fluorine atom, chlorine atom, bromine atom and iodine atom. In these atoms, chlorine atom or bromine atom is preferred. Chlorine atom is particularly preferred.

In the formulae in the present invention, $B^1$, $B^2$ and $B^3$, independently from each other, represent a protecting group for amino group. The protecting group for amino group is not particularly limited. For example, protecting groups described in Protecting Groups in Organic Chemistry, $2^{nd}$ edition (John Wiley & Sons, Inc., 1991) are usable. Among them, carbamato-type protecting groups are preferred because they can be easily removed. Examples of the carbamato type protecting groups include methoxycarbonyl group, ethoxycarbonyl group, t-butoxycarbonyl group, benzyloxycarbonyl group, fluorenylmethoxycarbonyl group and tetrahydrofuran-3-yloxycarbonyl group. Those protecting groups are not always removed and they may be used also as they are in the subsequent step depending on the intended compound in some cases. Examples of such groups include tetrahydrofuran-3-yloxycarbonyl group (European Patent No. 774453) and 3-protected hydroxy-2-methylbenzoyl group.

3-Oxazolidin-5-one derivatives represented by general formula (1) in the present invention can be easily produced by a known method such as i) a method wherein an N-protected amino acid is reacted with an aldehyde in the presence of an acid (see, for example, S. I. Hyun et al., Tetrahedron Lett. 1998, 39, 4299, and S. Karady et al., Tetrahedron Lett. 1984, 25, 39, 4337) or ii) a method wherein an α-amino acid or a salt thereof is reacted with an aldehyde and then the product is reacted with a reagent for protecting the amino group (see, for example, M. W. Walter et al., J. Org. Chem. 1998, 63, 5179 and M. W. Walter et al., Tetrahedron Lett. 1995, 36, 42, 7761).

The aldehydes are, for example, those of following general formula (6):

R—CHO (6)

wherein R represents hydrogen atom, a lower alkyl group having 1 to 6 carbon atoms or an aryl group having 6 to 15 carbon atoms.

Aldehydes preferably used in method i) include formaldehyde, lower alkylaldehydes such as acetaldehyde, and arylaldehydes such as benzaldehyde and anisaldehyde. Formaldehyde is particularly preferred. The acids used for the reaction are preferably organic acids such as benzenesulfonic acid, p-toluenesulfonic acid and pyridine p-toluenesulfonate (PPTS). The reaction solvents are preferably aprotic solvents such as benzene, toluene, tetrahydrofuran, dichloroethane, ethyl acetate and isopropyl acetate. Benzene or toluene is particularly preferred.

The aldehydes preferably used in method ii) are formaldehyde, lower alkyl aldehydes such as acetaldehyde and trimethylacetaldehyde, and arylaldehydes such as benzaldehyde and anisaldehyde.

Examples of the amino group-protecting reagents include alkoxycarbonylating reagents such as methoxycarbonyl chloride, ethoxycarbonyl chloride, isopropoxycarbonyl chloride, t-butoxycarbonyl chloride, benzyloxycarbonyl chloride, di-t-butyl dicarbonate and tetrahydrofuran-3-yloxycarbonyl chloride; acylating reagents such as acetic anhydride, acetyl chloride, benzoyl chloride and 3-protected hydroxy-2-methylbenzoyl chloride; and sulfonylating reagents such as methanesulfonyl chloride, trifluoromethanesulfonyl chloride, benzenesulfonyl chloride and p-toluenesulfonyl chloride.

The production process of the present invention can be employed for synthesizing optically active compounds by using an optically active α-amino acid or N-protected α-amino acid. Optically active amino acids are important in the field of medicines. Namely, optically active compounds (L- and D-compounds) are preferably used as the α-amino acids and N-protected α-amino acids. In particular, optically active phenylalanine and optically active phenylthioalanine and N-protected compounds of them are important starting materials of HIV protease inhibitors.

Now, the description will be made on the process for producing 5-chloromethyl-5-hydroxy-3-oxazolidine derivatives of general formula (2) by reacting a 3-oxazolidin-5-one derivative of general formula (1) with a lower alkyllithium and bromochloromethane or chloroiodomethane.

Halomethyllithiums in the present invention can be represented by following general formula (17):

(17)

wherein X is as defined above.

These halomethyllithiums can be formed by reacting an organic lithium compound such as methyllithium, n-butyllithium or sec-butyllithium with a dihalomethane such as bromochloromethane, chloroiodomethane or dibromomethane [see, for example, Encyclopedia of reagents for organic synthesis (John Wiley & Sons, Inc., 1995)]. A halomethyl ketone can be obtained by reacting a halomethyllithium, obtained as described above, with an ester (see, for example, R. Tarhouni et al., tetrahedron Lett. 1984, 25, 835; and J. Barluenga et al., J. Chem. Soc., Chem. Commun. 1994, 969). Also in the present invention, an organic lithium compound and a dihalomethane are added to a reaction solvent to form a corresponding halomethyllithium in the reaction system.

The halomethyllithiums are preferably chloromethyllithium and bromomethyllithium. Chloromethyllithium is particularly preferred. Chloromethyllithium is formed in the production of α-aminochloromethyl ketone [general formula (3) or (4) wherein X is chlorine atom], and bromomethyllithium is formed in the production of α-aminobromomethyl ketone [general formula (3) or (4) wherein X is bromine atom].

As known in the art, the halomethyllithiums are thermally unstable and, therefore, when a halomethyllithium is to be reacted with an ester, it is preferred to previously dissolve the ester and the dihalomethane in a solvent and then to add an organic lithium compound. The reaction may be conducted in the presence of a salt such as lithium chloride or lithium bromide.

The organic lithium compounds used in the present invention can be represented by, for example, following general formula (18):

(18)

wherein $R^1$ represents a lower alkyl group or aryl group.

The lower alkyl groups include linear or branched, saturated alkyl groups having 1 to 8 carbon atoms, and the aryl groups include phenyl group, naphthyl group, etc. Lower alkyllithiums of the above formula wherein $R^1$ represents a lower alkyl group are preferred. In particular, lower alkyllithiums of the above formula wherein $R^1$ represents a linear, saturated alkyl group having 1 to 6 carbon atoms such as methyl group, ethyl group, n-butyl group, sec-butyl group or n-hexyl group are preferred.

The dihalomethanes usable in the present invention are preferably bromochloromethane, chloroiodomethane and dibromomethane. Bromochloromethane and chloroiodomethane are particularly preferred. Bromochloromethane or chloroiodomethane is used for the production of α-aminochloromethyl ketone [general formula (3) wherein X represents chlorine atom] (when chloromethyllithium is formed). Dibromomethane is used for the production of α-aminobromomethyl ketone [general formula (3) or (4) wherein X represents bromine atom] (when bromomethyllithium is formed).

The amount of the organic lithium compound and dihalomethane used is not particularly limited, and they are used each in an amount of 1 to 2 equivalents per equivalent of the N-protected α-amino acid ester derivative. Although the amount of them may be larger than 2 equivalents, it is preferably 1 to 1.5 equivalents and more preferably 1.2 to 1.4 equivalents in the present invention because these reagents are expensive.

The reaction solvents are preferably ethers such as tetrahydrofuran, diethyl ether and t-butyl methyl ether. They are preferably used in the form of a mixture with a non-polar solvent such as toluene or hexane. The reaction rapidly proceeds at a temperature ranging from about –120° C. to 0° C. Usually, the reaction is completed in 5 to 60 minutes at –80° C. to –50° C. After the completion of the reaction, the reaction mixture may be treated with an aqueous potassium hydrogensulfate solution, aqueous ammonium chloride solution, phosphate buffer, water or the like. By treating the reaction mixture with an acid, the hydrolysis reaction in the subsequent step can be directly conducted.

Although the 5-halomethyl-5-hydroxy-3-oxazolidine derivative thus obtained can be purified by a method known in the art such as column chromatography, it may be used for the subsequent reaction without being separated or purified. When this compound is used for the production of compounds of general formula (3) or (4), the separation or purification thereof is usually not required.

A 3-oxazolidin-5-one derivative of general formula (1) is reacted with a halomethyllithium to obtain a 5-chloromethyl-5-hydroxy-3-oxazolidine derivative of general formula (2):

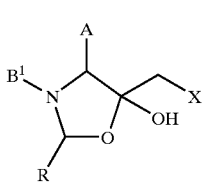

(2)

wherein X represents a halogen atom, and R, A and $B^1$ are as defined above.

Then, the description will be made on the process for producing an N-protected α-aminohalomethyl ketone of general formula (3) or an α-aminohalomethyl ketone of general formula (4) or a salt thereof by treating a 5-halomethyl-5-hydroxy-3-oxazolidine derivative of general formula (2) with an acid.

5-Halomethyl-5-hydroxy-3-oxazolidine derivatives of general formula (2) can be hydrolyzed by the reaction with an acid. The protecting group for the amino group is either removed or not removed depending on the relationship between the reaction conditions and the protecting group for the amino group.

The acids are not particularly limited, and they include inorganic acids such as hydrochloric acid, hydrobromic acid, hydroiodic acid and sulfuric acid; and organic acids such as formic acid, acetic acid and trifluoroacetic acid, and a combination of, for example, hydrobromic acid/acetic acid.

The solvents are not particularly limited, and they include water, methanol, ethanol, tetrahydrofuran, dioxane, ethyl acetate, dichloromethane, chloroform, toluene, hexane or a mixture of these solvents.

The N-protected α-aminohalomethyl ketone obtained when the protecting group for the amino group was not removed can be used after the purification by a method known in the art such as column chromatography or it can also be used for the subsequent reaction without the separation or purification.

The α-aminohalomethyl ketone obtained when the protecting group was removed can be converted to its salt by evaporating the solvent and crystallizing it under proper conditions. Various salts of the α-aminohalomethyl ketone can be obtained depending on the variety of the acid used. These salts can be used for the subsequent reaction as they are in the present invention. The salt can be converted to a free compound by the reaction with a corresponding amount of a base. However, the acidic salt is preferably used as it is because the free compound is more unstable than the salt.

When, for example, a 5-halomethyl-5-hydroxy-3-oxazolidine derivative is hydrolyzed with water or a water-containing solvent mixture (including a case wherein a reaction solution containing the 5-halomethyl-5-hydroxy-3-oxazolidine derivative is treated with an acid to directly conduct the hydrolysis reaction) and the alkoxycarbonylation reaction (such as methoxycarbonylation, ethoxycarbonylation, t-butoxycarbonylation or benzyloxycarbonylation reaction) of an α-aminohalomethyl ketone or reduction reaction of carbonyl group can be conducted in an aqueous solvent, the α-aminohalomethyl ketone solution can be directly used in the subsequent step.

Thus obtained N-protected α-aminohalomethyl ketone of general formula (3) or α-aminohalomethyl ketone of general formula (4) can be converted into an N-protected β-aminoepoxide by any of following reaction schemes (A), (B) and (C):

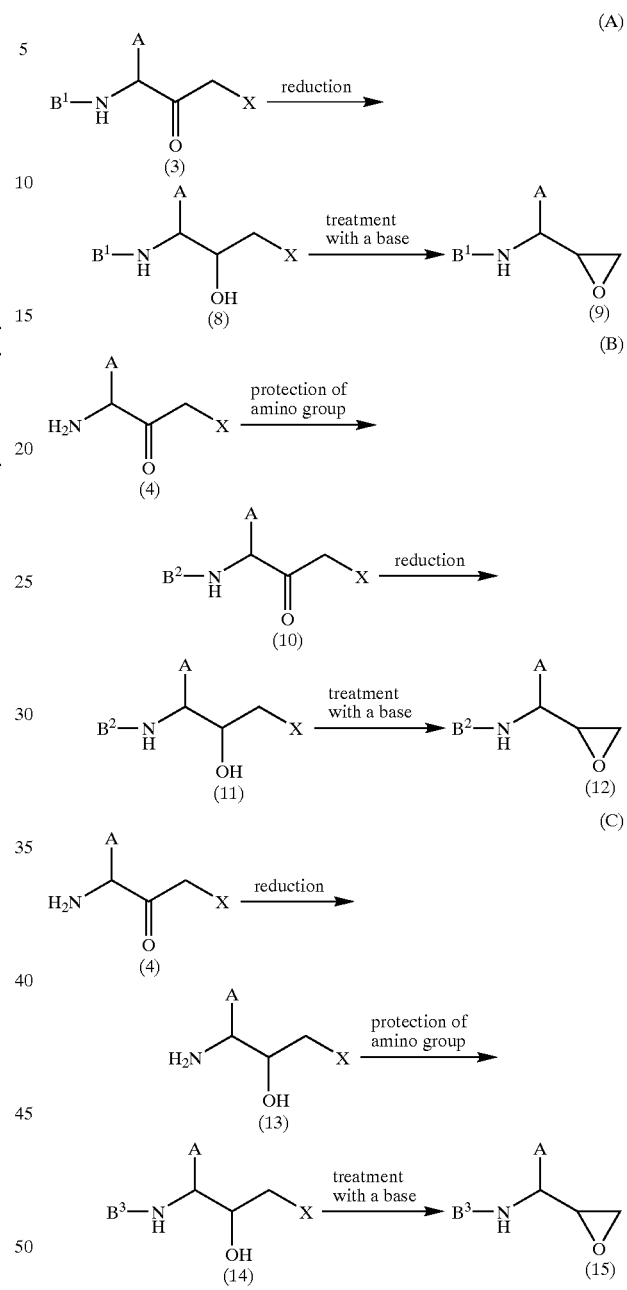

wherein A, $B^1$, $B^2$, $B^3$ and X are as defined above.

N-Protected-α-aminohalomethyl ketones of general formula (3) are known compounds usable as intermediates for HIV protease inhibitors (see, for example, D. P. Getman et al., J. Med. Chem., 1993, 36, 288; Y. Okada et al., Chem. Pharm. Bull., 1988, 36, 4794; EP 346867; and P. Raddatz et al., J. Med. Chem., 1991, 34, 3267). It is known that they can be converted into intermediates closer to the intended final product by two steps of known reactions as described below (see D. P. Getman et al., J. Med. Chem., 1993, 36, 288; WO 96/23756, J. P. KOKAI No. Hei 8-99947 and J. P. KOKAI No. Hei 8-99959).

Namely, an N-protected-α-aminohalomethyl ketone of general formula (3) can be converted into an N-protected-β-amino alcohol of general formula (8) by the reduction reaction of the carbonyl group, and then the alcohol can be then easily epoxidized under an alkaline condition to form an N-protected-β-amino epoxide of general formula (9).

The description will be made on the process for protecting amino group of an α-aminohalomethyl ketone of general formula (4) with a protecting group to form an N-protected-α-aminohalomethyl ketone of general formula (10).

Although α-aminohalomethyl ketones are stable under acidic conditions, they are unstable under basic conditions. Therefore, it is not preferred to conduct the reaction under basic conditions which are usually employed for the reaction for protecting the amino group in the synthesis of peptides.

Namely, reagents for protecting amino group such as alkoxycarbonylating reagents, acylating reagents and sulfonylating reagents must be used in the presence of a base. In the course of the reaction of them, the α-aminohalomethyl ketone is decomposed in a considerable amount to reduce the reaction yield. Therefore, for the efficient protection, the amino acid is preferably protected as follows:

Method 1: A reagent for protecting the amino group, such as an alkoxycarbonylating reagent, an acylating reagent or a sulfonylating reagent, is mixed with a base in a suitable solvent, and then a solution of an acidic salt of an α-aminohalomethyl ketone is added to the obtained mixture.

Method 2: A solution of a reagent for protecting the amino group, such as an alkoxycarbonylating reagent, an acylating reagent or a sulfonylating reagent, is mixed with a solution of an acidic salt of α-aminohalomethyl ketone, and then a base is added to the obtained mixture.

Particularly in the t-butoxycarbonylation, method 1 is preferred because t-butoxycarbonyl chloride or di-t-butyl dicarbonate used as the protecting reagent is unstable to acids.

Reagents for protecting amino group are not particularly limited. The reagents usable herein are not only those usually used for synthesizing peptides but also compounds having a functional group such as an alkoxycarbonyl group, an acyl group or sulfonyl group are usable for introducing an intended substituent.

Examples of the reagents for protecting amino group include alkoxycarbonylating reagents such as methoxycarbonyl chloride, ethoxycarbonyl chloride, isopropoxycarbonyl chloride, t-butoxycarbonyl chloride, benzyloxycarbonyl chloride, di-t-butyl dicarbonate and tetrahydrofuran-3-yloxycarbonyl chloride; acylating reagents such as acetic anhydride, acetyl chloride, benzoyl chloride and 3-protected hydroxy-2-methylbenzoyl chloride; and sulfonylating reagents such as methanesulfonyl chloride, trifluoromethanesulfonyl chloride, benzenesulfonyl chloride and p-toluenesulfonyl chloride. The protecting groups introduced by using those protecting reagents are not always removed, and they may the kept depending on the subsequent reaction steps and intended compounds.

The reaction solvents are, for example, water, methanol, ethanol, 2-propanol, t-butanol, acetone, tetrahydrofuran, diethyl ether, t-butyl methyl ether, ethyl acetate, isopropyl acetate, dichloromethane, chloroform and toluene, and mixtures of them. The solvent can be suitably selected depending on the reagent. When a solvent mixture is used, the mixture is either mono-layered or di-layered depending on the combination of the solvents. The reaction is preferably conducted in the di-layered solvent.

The α-aminohalomethyl ketones are preferably in the form of stable acidic salts thereof as described above. The solvents in which the acidic salts are to be dissolved are, for example, water, methanol and ethanol.

The α-aminohalomethyl ketone solution is added to the solvent containing the protecting reagent dissolved therein. The reaction time varies depending on the reagent and reaction temperature. In a typical example wherein di-t-butyl dicarbonate is used for the t-butylcarbonylation, the reaction is completed in several minutes to about 2 hours at 40° C. or in several minutes to about 10 hours at room temperature.

The bases are organic bases such as triethylamine, diisopropylethylamine, dicyclohexylmethylamine, N-methylmorpholine, N-ethylmorpholine, pyridine, 2,6-lutidine, 2,4,6-collidine, 4-picoline and N-ethylpiperidine; and inorganic bases such as sodium hydroxide, potassium hydroxide, sodium carbonate, potassium carbonate, sodium hydrogencarbonate, potassium hydrogencarbonate, disodium hydrogenphosphate and dipotassium hydrogenphosphate.

When the reagent for protecting amino group is mixed with the base in a suitable solvent and then a solution of an acidic salt of α-aminohalomethyl ketone is added to the solution (method 1 described above), the base is preferably sodium hydrogencarbonate, potassium hydrogencarbonate, triethylamine or diisopropylethylamine. The base is particularly preferably triethylamine or diisopropylethylamine. The amount of the base to be added to the solution of the protecting reagent is preferably 0.8 to 1.2 equivalents, more preferably around 1 equivalent, per equivalent of the acid (including the acid used for forming the salt) contained in the solution of the acidic salt of α-aminohalomethyl ketone.

The α-aminohalomethyl ketone solution is added to the solvent containing the protecting reagent dissolved therein. The reaction time varies depending on the reagent and reaction temperature. For example, when di-t-butyl dicarbonate is used for the t-butylcarbonylation, the reaction is completed in several minutes to about 2 hours at 40° C. or in several minutes to about 10 hours at room temperature.

When a solution of a reagent for protecting the amino group, such as an alkoxycarbonylating reagent, an acylating reagent or a sulfonylating reagent is mixed with a solution of an acidic salt of α-aminohalomethyl ketone and then a base is added to the obtained mixture (method 2 described above), the base is preferably sodium hydrogencarbonate, potassium hydrogencarbonate, triethylamine or diisopropylethylamine. The amount of the base to be added is preferably 0.8 to 1.2 equivalents, more preferably around 1 equivalent, per equivalent of the acid (including the acid used for forming the salt) contained in the solution of the acidic salt of α-aminohalomethyl ketone.

The base is used in the form of a solution in a suitable solvent. The reaction time varies depending on the reagent and reaction temperature. For example, when benzyloxycarbonyl chloride is used for the benzyloxycarbonylation, the reaction is completed in about 10 minutes to about 2 hours at room temperature.

Then the reaction product is extracted from the reaction solution with a solvent such as ethyl acetate, diethyl ether, toluene, isopropyl acetate, tert-butyl methyl ether, dichloromethane or chloroform. Then,if necessary, the obtained solution is concentrated (or evaporated). If necessary, a solvent such as methanol, ethanol, 2-propanol, acetonitrile, tetrahydrofuran, hexane, heptane or acetone is added to the product. The obtained solution is heated to about 40 to 80° C. The N-protected α-aminohalomethyl ketone (7) can be obtained in solid form by the crystallization by cooling to a temperature of −20° C. to room temperature or by a chromatography. The product may be used for the subsequent reaction without being separated or purified.

The solvent containing the protecting reagent dissolved therein contains a base in an amount of preferably 0.8 to 1.2 equivalents, more preferably around 1 equivalent, per equivalent of the acid contained in the solution of the acidic salt of α-aminohalomethyl ketone.

As described above, an N-protected-α-aminohalomethyl ketone of general formula (10) can be converted to an N-protected-β-amino alcohol of general formula (11) by the reduction reaction of the carbonyl group, and then the alcohol can be easily epoxidized under an alkaline condition to form an N-protected-β-aminoepoxide of general formula (12).

The description will be made with reference to an example wherein sodium borohydride is used as the reducing agent.

Although the amount of sodium borohydride to be added is not particularly limited, it is usually used in an amount of at least 0.5 mol per mol of the starting compound.

The reaction solvents are protic solvents such as water and alcohols. Alcohols or mixed solvents of an alcohol and at least one of other solvents are preferred. The alcohols are, for example, methanol, ethanol, 1-propanol, 2-propanol, 1-butanol, 2-butanol and 1,2-dimethylpropanol. Methanol and ethanol are particularly preferred. A combination of these alcohols is also usable. The solvents usable in the form of a mixture with the alcohols are, for example, ethyl acetate, isopropyl acetate, dichloromethane, ether, tert-butyl methyl ether, tetrahydrofuran, 1,4-dioxane, benzene, toluene and water. Ethyl acetate, toluene and water are particularly preferred.

Although the reaction temperature is not particularly limited, it is usually not higher than room temperature and is preferably –78° C. to room temperature, more preferably –78° C. to 5° C. The reaction time, which is also not particularly limited, is preferably about 10 minutes to 10 hours.

The reaction is usually conducted under stirring. After the completion of the reaction, the reaction is usually terminated with an acid. The acids preferably used are hydrochloric acid, sulfuric acid, acetic acid, citric acid and an aqueous potassium hydrogensulfate solution. Although the amount of the acid used is not particularly limited, it is preferably at least 1 molar equivalent per molar equivalent of sodium borohydride.

Then the reaction product is extracted from the reaction solution with a solvent such as ethyl acetate, diethyl ether, toluene, isopropyl acetate, tert-butyl methyl ether, dichloromethane or chloroform. If necessary, the obtained solution is concentrated (or evaporated). If necessary, a solvent such as methanol, ethanol, 2-propanol, acetonitrile, tetrahydrofuran, hexane, heptane or acetone is added thereto and the obtained solution is heated to about 40 to 80° C. and then cooled to –20° C. to room temperature to conduct the crystallization or the solution is subjected to a chromatography to obtain the N-protected β-aminoalcohol in solid form. Crystalline N-protected β-aminoalcohol can also be obtained by concentrating the reaction solution if necessary, adding water thereto if necessary, directly cooling the reaction solution under the above-described conditions to form crystals and washing the obtained crystals with water or an organic solvent.

An N-protected β-aminoepoxide of general formula (9) can be obtained by treating the obtained N-protected β-aminoalcohol of general formula (8) with a base.

The bases are, for example, potassium hydroxide, sodium hydroxide, potassium carbonate, sodium carbonate, sodium methoxide, sodium ethoxide, potassium tert-butoxide and sodium hydride. Sodium hydroxide and potassium carbonate are particularly preferred. The reaction solvents are protic solvents such as methanol, ethanol, 1-propanol, 2-propanol, 1-butanol, 2-butanol, 1,2-dimethylpropanol and water and aprotic solvents such as acetone, tetrahydrofuran and acetonitrile. They are used either alone or in the form of a mixture of them. In those solvents, ethanol, a solvent mixture of 2-propanol and water and a solvent mixture of ethanol and water are particularly preferred.

The amount of the base, which varies depending on the combination of the base and the solvent, is 1 to 10 equivalents, preferably 1 to 5 equivalents. The reaction temperature which also varies depending on the combination of the base and the solvent, is –10 to –80° C., preferably 0 to –60° C. The reaction time, which is not particularly limited, is preferably about 10 minutes to 50 hours.

The reaction is usually conducted under stirring. After the completion of the reaction, the reaction may be terminated with an acid. The acids preferably used are hydrochloric acid, sulfuric acid, acetic acid, citric acid and an aqueous potassium hydrogensulfate solution.

Then the reaction product is extracted from the reaction solution with a solvent such as ethyl acetate, diethyl ether, toluene, isopropyl acetate, tert-butyl methyl ether, dichloromethane or chloroform. If necessary, the obtained solution is concentrated. If necessary, a solvent such as methanol, ethanol, 2-propanol, acetonitrile, tetrahydrofuran, hexane, heptane or acetone is added thereto and the obtained solution is heated, if necessary, to room temperature to about 50° C. and then cooled to –20° C. to room temperature to conduct the crystallization or it is subjected to a chromatography to obtain the solid N-protected β-amino epoxide. Crystalline N-protected β-amino epoxide can also be obtained by concentrating the reaction solution if necessary, adding water thereto if necessary, directly cooling the reaction solution under the above-described conditions to form crystals and washing the obtained crystals with water or an organic solvent.

An α-aminohalomethyl ketone of general formula (4) can be converted into a β-aminoalcohol of general formula (13) by reducing the carbonyl group of the ketone. The concrete description will be given below.

A reducing agent is previously dissolved or suspended in a suitable solvent, and then a solution of an acidic salt of the α-aminohalomethyl ketone is added thereto.

The solvent in which the reducing agent is to be dissolved or suspended is not particularly limited. It is preferably a protic solvent such as water, methanol or ethanol.

The solvent in which α-aminohalomethyl ketone is to be dissolved is, for example, water, methanol or ethanol. The α-aminohalomethyl ketone is preferably used in the form of a salt with an acid.

The reducing agent is not particularly limited. However, when the reaction is conducted in an aqueous solution, the reducing agent is particularly preferably sodium borohydride or sodium cyanoborohydride. Although the amount of the reducing agent is not particularly limited, it is usually used in an amount of at least 0.5 molar equivalent per molar equivalent of the starting compound.

For inhibiting the decomposition of the reducing agent with the acid, it is preferred to add a base together with the reducing agent. The amount of the base to be added to the solution of the reducing agent is preferably 1 to 2 equivalents, more preferably around 1 equivalent, per equivalent of the acid (including the acid used for forming the salt) contained in the solution of the acidic salt of α-aminohalomethyl ketone.

The bases are sodium hydroxide, potassium hydroxide, sodium carbonate, potassium carbonate, sodium hydrogencarbonate, potassium hydrogencarbonate, etc.

The reaction temperature is not particularly limited. For example, when sodium borohydride is used, the reaction is conducted at a temperature of preferably −20 to 100° C., particularly 0° C. to room temperature.

The reaction is usually conducted under stirring. After the completion of the reaction, the reaction is usually terminated with an acid. The acids preferably used are hydrochloric acid, sulfuric acid, acetic acid, citric acid and an aqueous potassium hydrogensulfate solution. Although the amount of the acid used is not particularly limited, it is preferably at least 1 molar equivalent per molar equivalent of sodium borohydride.

After adding water to the reaction mixture, the aqueous layer is washed with a suitable organic solvent such as ethyl acetate, isopropyl acetate, dichloromethane, chloroform or toluene to transfer an aldehyde and a ketone formed as by-products by the hydrolysis into the organic layer. The obtained aqueous layer is concentrated. An alcohol is added to the obtained concentrate, an insoluble matter is filtered out and then product is crystallized under suitable conditions (e. g. crystallization by cooling or crystallization by concentration) from an alcohol or a solvent mixture of the alcohol and one or more solvents to obtain the β-aminoalcohol in the form of a salt thereof. The alcohols are, for example, methanol, ethanol and 2-propanol. The solvents usable in the form of a mixture with the alcohols are, for example, ethyl acetate, isopropyl acetate, dichloromethane, diethyl ether, tert-butyl methyl ether, tetrahydrofuran, 1,4-dioxane, benzene, toluene and water.

β-Aminoalcohols of general formula (13) are well-known compounds usable as, for example, intermediates for HIV protease inhibitors (see, for example, P. L. Beaulieu et al., J. Org. Chem., 1996, 61, 3635). It is known that they can be converted into intermediates closer to the intended final product by two steps of known reactions as described below.

Namely, β-aminoalcohols of general formula (13) are converted to N-protected β-aminoalcohols of general formula (14) by protecting the amino group of the former by an ordinary method. The N-protected β-aminoalcohols can be easily epoxidized under alkaline conditions to form N-protected β-aminoepoxides of general formula (15).

The compounds in the present invention also include racemic compounds and both optically active compounds. When an N-protected α-amino acid of general formula (5) or an α-amino acid of general formula (7) is used, a compound of general formula (3) or (4) obtained by the process of the present invention maintains its optical activity. Further, compounds of general formulae (7) to (15) produced from the compounds of general formula (3) or (4) also maintain their optical activity. Therefore, the process of the present invention is extremely useful for the synthesis of intermediate compounds for medicines.

The following Examples will further illustrate the present invention.

REFERENTIAL EXAMPLE 1

Process for Producing (4S)-N-tert-butoxycarbonyl-4-phenylmethyloxazolidin-5-one

Tert-butoxycarbonyl-L-phenylalanine (20.00 g), paraformaldehyde (6.04 g) and pyridinium p-toluenesulfonate (0.95 g) were added to toluene (200 ml), and they were stirred under heating and reflux for 30 minutes. The reaction mixture was cooled to room temperature and washed with a saturated aqueous sodium hydrogencarbonate solution and saturated aqueous sodium chloride solution. The obtained toluene layer was dried over anhydrous sodium sulfate and then sodium sulfate was removed. The solvent was evaporated under reduced pressure. The concentrated solution was cooled to room temperature to crystallize the product. The crystals were separated and dried to obtain intended (4S)-N-tert-butoxycarbonyl-4-phenylmethyloxazolidin-5-one (15.10 g) (yield: 72%).

1H-NMR(CDCl3, 300 MHz) δ ppm: 1.51 (9H, s), 3.15 (d, 1H), 3.20–3.52 (m, 1H), 4.13–4.38 (m, 1H), 4.49 (bs, 1H), 5.06–5.38 (m, 1H), 7.12–7.22 (m, 2H), 7.22–7.35 (m, 3H)

mass spectrum m/e: 278.2 (MH+)

$[\alpha]_D^{20}$=+153.4° (c=0.7, CH$_2$Cl$_2$)

REFERENTIAL EXAMPLE 2

Process for Producing (4S)-N-benzyloxycarbonyl-4-phenylthiomethyloxazolidine-5-on (2S)-2-benzyloxycarbonylamino-3-phenylthiopropionic acid 5.00 g), paraformaldehyde (1.21 g) and p-toluenesulfonic acid monohydrate (0.15 g) were added to benzene (50 ml), and they were stirred under heating and reflux for 1.5 hours. The reaction mixture was cooled to room temperature and washed with a saturated aqueous sodium hydrogencarbonate solution and saturated aqueous sodium chloride solution. The obtained toluene layer was dried over anhydrous magnesium sulfate and then magnesium sulfate was removed. The solvent was evaporated under reduced pressure to obtain intended (4S)-N-benzyloxycarbonyl-4-phenylthiomethyloxazolidin-5-one (5.18 g) (yield: 100%).

1H-NMR (CDCl3, 300 MHz) δ ppm: 3.36 (d, 1H), 3.60–4.02 (m, 1H), 4.50–4.64 (bs, 1H), 4.78–5.51 (m, 4H), 7.11–7.46 (m, 10H)

EXAMPLE 1

Process for Producing (4S)-N-tert-butoxycarbonyl-5-chloromethyl-5-hydroxy-4-phenylmethyloxazolidine (4S)-N-tert-butoxycarbonyl-4-phenylmethyloxazolidin-5-one (0.34 g) and bromochloromethane (0.10 ml) were added to dehydrated tetrahydrofuran (12 ml). After cooling to −78° C., 1.53 M solution (1.03 ml) of n-butyllithium in hexane was added to the obtained mixture, and they were stirred for 1 hour. 10% aqueous potassium hydrogensulfate solution was added to the reaction mixture to terminate the reaction. The temperature of the reaction mixture was elevated to room temperature. After the extraction with ethyl acetate twice, the obtained ethyl acetate layer was dried over anhydrous magnesium sulfate and then magnesium sulfate was removed. The solvent was evaporated under reduced pressure to obtain intended (4S)-N-tert-butoxycarbonyl-5-chloromethyl-5-hydroxy-4-phenylmethyloxazolidine (0.40 g) in a yield of 100%.

A part of the product was treated with 6 N hydrochloric acid to form (S)-3-amino-1-chloro-4-phenyl-2-butanone hydrochloride. According to HPLC analysis with an optically active column, the optical purity was confirmed to be >99% e.e.

1H-NMR (CDCl3, 300 MHz) δ ppm: 1.48 (s, 9H), 3.02 (dd, J=10.1, 13.2 Hz, 1H), 3.24–3.34 (m, 3H), 3.80 (d, J=11.5 Hz, 1H), 3.93 (dd, J=4.5, 10.0 Hz, 1H), 4.87 (d, J=4.7 Hz, 1H), 5.17 (bs, 1H), 7.18–7.33 (m, 5H)

$[\alpha]_D^{20}$=−22.8° (c=1.0, CH2Cl2)

EXAMPLE 2

Process for Producing (S)-3-amino-1-chloro-4-phenyl-2-butanone Hydrochloride (4S)-N-tert-butoxycarbonyl-4-phenylmethyloxazolidin-5-one (1.00 g) and bromochloromethane (0.31 ml) were added to dehydrated tetrahydrofuran (36 ml). After cooling to −78° C., 1.53 M solution (3.07 ml) of n-butyllithium in hexane was added to the obtained mixture, and they were stirred for 40 minutes. 6 N Hydrochloric acid was added to the reaction mixture to terminate the reaction. The temperature of the reaction mixture was elevated to room temperature. The reaction mixture was concentrated to a half volume, stirred at 50° C. for 1 hour and cooled to room temperature. After the addition of isopropyl acetate followed by the extraction with water twice, the obtained aqueous solution was analyzed by HPLC to find that intended (S)-3-amino-1-chloro-4-phenyl-2-butanone hydrochloride (0.65 g) was obtained in a yield of 77%. According to HPLC analysis with an optically active column, the optical purity of (S)-3-amino-1-chloro-4-phenyl-2-butanone hydrochloride thus obtained was confirmed to be >99% e.e.

For obtaining various spectral data, a part of the obtained aqueous solution was concentrated under reduced pressure. Ethanol was added to the concentrate. The solvent was evaporated again under reduced pressure. After the filtration, the filtrate was concentrated and then the product was crystallized from ethanol and tert-butyl methyl ether to obtain crystals of (3S)-3-amino-1-chloro-4-phenyl-2-butanone hydrochloride.

1H-NMR (d6-DMSO, 300 MHz) δ ppm: 3.04 (dd, J=7.1, 15.2 Hz, 1H), 3.22 (dd, J=7.1, 15.2 Hz, 1H), 4.54 (t, J=7.1 Hz, 1H), 4.58 (d, J=17.3 Hz, 1H), 4.70 (d, J=17.3 Hz, 1H), 7.28–7.41 (m, 5H), 8.37 (bs, 3H)

mass spectrum m/e: 198.0 (MH+)

$[\alpha]_D^{25}$=+30.20 (c=0.5, $H_2O$)

optical purity: >99.5% e.e.

EXAMPLE 3

Process for Producing (3S)-3-tert-butoxycarbonylamino-1-chloro-4-phenyl-2-butanone Di-tert-butyl dicarbonate (1.39 g) and sodium hydrogencarbonate (0.34 g) were dissolved in 50% aqueous methanol solution (22 ml). An aqueous solution of (3S)-3-amino-1-chloro-4-phenyl-2-butanone hydrochloride (0.94 g) was added to the obtained solution, and they were stirred at 40° C. for 1.5 hours. After the extraction with ethyl acetate twice, the obtained ethyl acetate layer was dried over anhydrous magnesium sulfate. Magnesium sulfate was removed. The solvent was evaporated under reduced pressure. Crystals formed by the crystallization with ethyl acetate and hexane were taken by filtration and then dried to obtain (3S)-3-tert-butoxycarbonylamino-1-chloro-4-phenyl-2-butanone (0.84 g) in a yield of 70%.

The obtained crystals and the reaction mixture were analyzed by HPLC with an optically active column to confirm that the product had an optical purity of >99.5% e.e.

1H-NMR (CDCl3, 300 MHz) δ ppm: 1.41 (s, 9H), 3.00(dd, J=6.9, 13.8 Hz), 3.08 (dd, J=6.9, 13.8 Hz, 1H), 3.98 (d, J=16.2 Hz, 1H), 4.17 (d, J=16.2 Hz, 1H), 4.68 (q, J=6.9 Hz, 1H), 5.02 (bd, J=6.9 Hz, 1H), 7.16 (m, 2H), 7.26–7.36 (m, 3H)

mass spectrum m/e: 296.1 (M−H−)

$[\alpha]_D^{25}$=−55.7° (c=1, EtOH)

EXAMPLE 4

Process for Producing (2S,3S)-3-tert-butoxycarbonylamino-1-chloro-2-hydroxy-4-phenylbutane (3S)-3-tert-butoxycarbonylamino-1-chloro-4-phenyl-2-butanone (0.57 g) was added to a mixed solution of methanol (9 ml) and methylene chloride (9 ml). Sodium borohydride (92 mg) was added in portions to the obtained mixture under cooling with ice, and they were stirred for 1 hour. Acetic acid (0.59 ml) was added to the reaction mixture to terminate the reaction. After the addition with water followed by the extraction with isopropyl acetate twice, the obtained solution in isopropyl acetate was washed with 5% aqueous sodium hydrogencarbonate solution twice and saturated aqueous sodium chloride solution once.

The obtained solution in isopropyl acetate was analyzed by HPLC to find that 3-tert-butoxycarbonylamino-1-chloro-2-hydroxy-4-phenylbutane (0.57 g) was obtained in a yield of 83%. The ratio of the intended (2S, 3S) compound to the isomer thereof (2R, 3S) was (2S, 3S)/(2R, 3S)=83.2:16.8.

A part of the solvent was evaporated from a part of the solution of (2S, 3S)-3-tert-butoxycarbonylamino-1-chloro-2-hydroxy-4-phenylbutane in isopropyl acetate under reduced pressure. Ethyl acetate was added to the residue, and they were heated to obtain a solution. n-Hexane was added to the obtained solution. After the crystallization under cooling with ice, crystals of (2S, 3S)-3-tert-butoxycarbonylamino-1-chloro-2-hydroxy-4-phenylbutane were obtained. The spectral data were obtained. The ratio of the intended product (2S, 3S) to the isomer thereof (2R, 3S) in the obtained crystals was as follows: (2S, 3S)/(2R, 3S)=92.3:7.7.

1H-NMR (CDCl3, 300 MHz) δ ppm: 1.37 (s, 9H), 2.85–2.98 (m, 1H), 3.00 (dd, J=5.8, 13.9 Hz, 1H), 3.16 (bs, 1H), 3.59 (dd, J=11.6, 17.4 Hz, 1H), 3.59–3.71 (m, 1H), 3.77–3.97 (bm, 2H), 4.57 (bs, 1H), 7.19–7.35 (m, 5H)

mass spectrum m/e: 322 (M+Na+)

$[\alpha]_D^{20}$=−23.6° (c=0.5, $CH_2Cl_2$)

EXAMPLE 5

Process for Producing (2S,3S)-3-tert-butoxycarbonylamino-1,2-epoxy-4-phenylbutane (2S,3S)-3-tert-butoxycarbonylamino-1-chloro-2-hydroxy-4-phenylbutane (0.40 g) and potassium carbonate (0.37 g) were added to methanol (8 ml), and they were stirred at room temperature for 6 hours. The inorganic salt was removed from the reaction mixture by the filtration and then the filtrate was analyzed by HPLC to confirm that intended (2S,3S)-3-tert-butoxycarbonylamino-1,2-epoxy-4-phenylbutane (0.35 g) was obtained in a yield of 100%. The filtrate was concentrated under reduced pressure. Water was added to the residue. After the extraction with methylene chloride, the obtained methylene chloride layer was washed with 20% aqueous citric acid solution. The solvent was evaporated under reduced pressure. Ethyl acetate (2 ml) was added to the residue and they were heated to obtain a solution, which was cooled to room temperature to conduct the crystallization. n-Hexane (4 ml) was added thereto and they were stirred under cooling on ice. The crystals were separated and dried to obtain intended crystals of (2S,3S)-3-tert-butoxycarbonylamino-1,2-epoxy-4-phenylbutane (0.30 g) in a yield of 85%.

1H-NMR (CDCl3, 300 MHz) δ ppm: 1.38 (s, 9H), 2.73–2.81 (m, 2H), 2.84–3.01 (m, 3H), 3.69 (bs, 1H), 4.54 (d, J=8.2 Hz, 1H), 7.21–7.31 (m, 5H 13C-NMR (CDCl3,75 MHz) δ ppm: 28.3, 37.6, 46.8, 52.6, 53.2, 79.6, 126.6, 128.5, 129.4, 136.7, 155.2 mass spectrum m/e: 286 (M+Na+)

$[\alpha]_D^{20} = -15.4°$ (c=2.2, CH$_2$Cl$_2$)

EXAMPLE 6

Process for Producing (3S)-3-benzyloxycarbonylamino-1-chloro-4-phenyl-2-butanone (4S)-N-benzyloxycarbonyl-2-(p-methoxyphenyl)-4-phenylmethyloxazolidin-5-one (Tetrahedron Lett. 1995, 36, 42, 7761) (700 mg) and bromochloromethane (0.142 ml) were added to dehydrated tetrahydrofuran (16.8 ml), and they were cooled to −78° C. 1.54 Mn-butyllithium solution (1.42 ml) in hexane was added to the obtained mixture, and they were stirred for 33 minutes. 5% aqueous potassium hydrogensulfate solution was added to the reaction mixture to terminate the reaction. After the extraction with ethyl acetate at room temperature twice followed by drying over anhydrous magnesium sulfate, magnesium sulfate was removed. The obtained solution in ethyl acetate was analyzed by HPLC to find that (3S)-3-benzyloxycarbonylamino-1-chloro-4-phenyl-2-butanone (347 mg) was obtained in a yield of 62%.

EXAMPLE 7

Process for Producing (3S)-3-tert-butoxycarbonylamino-1-chloro-4-phenyl-2-butanone Di-tert-butyl dicarbonate (4.64 g) and triethylamine (5.28 ml) were dissolved in toluene (81.9 ml). An aqueous solution (45.60 g) of (3S)-3-amino-1-chloro-4-phenyl-2-butanone hydrochloride (3.83 g) was added dropwise to the obtained solution for a period of 10 minutes. After stirring at room temperature for 1 hour, the reaction mixture wa to 40° C. and the reaction was cnoducted for additional 1 hour. The reaction mixture was cooled to room temperature, and the aqueous layer was separated. The resultant toluene layer was washed with 2 N hydrochloric acid and saturated aqueous sodium chloride solution and then dried over anhydrous magnesium sulfate. Magnesium sulfate was removed. The obtained toluene layer was analyzed by HPLC to find that (3S)-3-tert-butoxycarbonylamino-1-chloro-4-phenyl-2-butanone (3.94 g) was obtained in a yield of 81%. The solvent was evaporated under reduced pressure, and n-hexane and 2-propanol were added to the residue. They were heated to 50° C. to obtain a homogeneous solution, which was cooled to room temperature, stirred for 1 hour, then cooled to 5° C. and stirred for 1 hour. Crystals thus formed were taken by the filtration and then dried to obtain (3S)-3-tert-butoxycarbonylamino-1-chloro-4-phenyl-2-butanone (2.98 g) in a crystallization rate of 75%.

EXAMPLE 8

Process for Producing (3S)-3-benzyloxycarbonylamino-1-chloro-4-phenyl-2-butanone (3S)-3-Amino-1-chloro-4-phenyl-2-butanone hydrochloride (100 mg) was dissolved in water (4.3 ml). A solution (5.3 ml) of benzyl chloroformate (0.794 ml) in toluene was added to the obtained solution. Further, an aqueous solution (1.0 ml) of sodium hydrogencarbonate (71.9 mg) was added dropwise to the obtained mixture. They were stirred at room temperature for 50 minutes to conduct the reaction and then the aqueous layer was separated. The obtained toluene layer was analyzed by HPLC to find that (3S)-3-benzyloxycarbonylamino-1-chloro-4-phenyl-2-butanone (118 mg) was obtained in a yield of 83%.

EXAMPLE 9

Process for Producing (3S)-3-methoxycarbonylamino-1-chloro-4-phenyl-2-butanone (3S)-3-Amino-1-chloro-4-phenyl-2-butanone hydrochloride (2.0 g) was dissolved in water (34 ml). A solution (50 ml) of methyl chloroformate (0.858 ml) in toluene was added to the obtained solution. Further, an aqueous solution (15 ml) of sodium hydrogencarbonate (1.44 g) was added dropwise to the obtained mixture. They were stirred at room temperature for 1 hour to conduct the reaction. After the extraction with toluene twice and with ethyl acetate twice, the organic layers were combined together. The solvents were evaporated under reduced pressure. n-Hexane and 2-propanol were added to the residue. The obtained mixture was heated to 50° C. to obtain a homogeneous solution, which was cooled to 10° C. to form crystals. The crystals were taken by the filtration, washed with cold 2-propanol (6 ml) and then dried to obtain (3S)-3-methoxycarbonylamino-1-chloro-4-phenyl-2-butanone (1.70 g) in a yield of 78%.

$^1$H-NMR (CDCl$_3$) δ ppm: 2.97–3.14 (m, 2H), 3.66 (s, 3H), 3.98 (d, J=16.0 Hz, 1H), 4.15 (d, J=16.0 Hz, 1H), 4.75 (q, J=7.2 Hz, 1H), 5.21 (bd, 1H), 7.12–7.18 (m, 2H), 7.23–7.37 (m, 3H)

EXAMPLE 10

Process for Producing (2S,3S)-3-tert-butoxycarbonylamino-1-chloro-2-hydroxy-4-phenylbutane Ethyl acetate (4.2 ml) and ethanol (16.7 ml) were added to (3S)-3-tert-butoxycarbonylamino-1-chloro-4-phenyl-2-butanone (2.08 g). Sodium borohydride (133 mg) was added in portions to the obtained mixture at −10° C., and they were stirred for 1 hour 40 minutes. Acetic acid (0.40 ml) was added to the reaction mixture to terminate the reaction. The reaction mixture was slowly heated to 60° C. for the duration of 1 hour and then stirred at 60° C. for 30 minutes. The reaction mixture was slowly cooled to −10° C. for the duration of 1 hour 50 minutes and then stirred at −10° C. for 6 hours. The crystals thus formed were taken by the filtration, washed with 0° C. water and dried under reduced pressure to obtain intended (2S,3S)-3-tert-butoxycarbonylamino-1-chloro-2-hydroxy-4-phenylbutane (1.52 g).

EXAMPLE 11

Process for Producing (2S,3S)-3-tert-butoxycarbonylamino-1,2-epoxy-4-phenylbutane (2S,3S)-3-tert-butoxycarbonylamino-1-chloro-2-hydroxy-4-henylbutane (3.57 g) was added to a mixed solution (35.7 ml) of ethanol and water (97:3), and they were stirred at 27° C. for 22 hours and then at 33° C. for 4 hours. 11.3% aqueous citric acid solution (40.3 g) was added to the obtained mixture, and they were cooled to −10° C. The crystals thus formed were taken by the filtration, washed with water (35.7 ml) and dried under reduced pressure to obtain intended (2S,3S)-3-tert-butoxycarbonylamino-1,2-epoxy-4-phenylbutane (2.88 g) in a yield of 95%.

EXAMPLE 12

Process for Producing (2S,3S)-3-tert-butoxycarbonylamino-1,2-epoxy-4-phenylbutane 2-Propanol (2.4 ml) was added to (2S,3S)-3-tert-butoxycarbonylamino-1-chloro-2-hydroxy-4-phenylbutane (300 mg). After cooling to 4° C., 4 mol/l aqueous sodium hydroxide solution (0.375 ml) and water (0.225 ml) were added to the obtained mixture, and they were stirred at 4° C. for 7 hours. 13.7% aqueous citric acid solution (695 mg) was added to the reaction mixture. After the extraction with tert-butyl methyl ether, the obtained organic layer was washed with water and analyzed by HPLC to find that intended (2S,3S)-3-tert-butoxycarbonylamino-1,2-epoxy-4-phenylbutane (230 mg)was obtained in an yield of 87%.

According to the present invention, α-aminohalomethyl ketones, N-protected α-aminohalomethyl ketones and related substances can be efficiently produced at a low cost from N-protected α-amino acids or α-amino acids. Thus, various compounds useful as intermediates for medicines can be produced. Because the optical activity can be kept, the process of the present invention is particularly suitable for producing intermediates of medicines having structures derived from optically active amino acids.

What is claimed is:

1. A process for producing N-protected β-aminoalcohols of following formula (8), or a salt thereof:

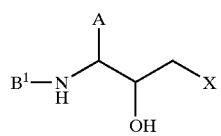

(8)

wherein A represents an unsubstituted or substituted alkyl group having 1 to 10 carbon atoms, aryl group having 6 to 15 carbon atoms or aralkyl group having 7 to 20 carbon atoms, an unsubstituted or substituted alkyl group having 1 to 10 carbon atoms which contains a hetero atom in the carbon skeleton, an aryl group having 6 to 15 carbon atoms which contains a hetero atom in the carbon skeleton, or an aralkyl group having 7 to 20 carbon atoms which contains a hetero atom in the carbon skeleton; $B^1$ represents a protecting group for the amino group; and X represents a halogen atom, which comprises producing an N-protected α-aminohalomethyl ketone of formula (3), or a salt thereof,

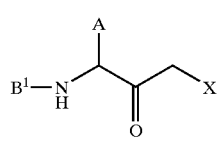

(3)

wherein A, $B^1$, and X are as defined above, and then reducing this ketone, wherein said producing an N-protected α-aminohalomethyl ketone of formula (3) comprises:

reacting a 3-oxazolidin-5-one derivative of the following (1):

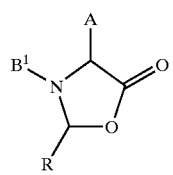

wherein R represents an unsubstituted or substituted aryl group or lower alkyl group, or a hydrogen atom, and A and $B^1$ are as defined above; with a halomethyl lithium to produce a reaction product;

and then treating the reaction product with an acid.

2. A process for producing N-protected β-aminoepoxides of following formula (9):

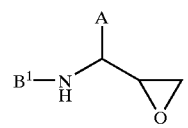

(9)

wherein A represents an unsubstituted or substituted alkyl group having 1 to 10 carbon atoms, aryl group having 6 to 15 carbon atoms or aralkyl group having 7 to 20 carbon atoms, an unsubstituted or substituted alkyl group having 1 to 10 carbon atoms which contains a hetero atom in the carbon skeleton, an aryl group having 6 to 15 carbon atoms which contains a hetero atom in the carbon skeleton, or an aralkyl group having 7 to 20 carbon atoms which contains a hetero atom in the carbon skeleton; and $B^1$ represents a protecting group for the amino group, which comprises producing an N-protected β-amino alcohol of formula (8) by the process of claim 1, and then treating this alcohol with a base.

3. A process for producing N-protected β-aminoalcohols of following formula (11):

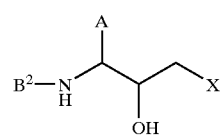

(11)

wherein A represents an unsubstituted or substituted alkyl group having 1 to 10 carbon atoms, aryl group having 6 to 15 carbon atoms or aralkyl group having 7 to 20 carbon atoms, an unsubstituted or substituted alkyl group having 1 to 10 carbon atoms which contains a hetero atom in the carbon skeleton, an aryl group having 6 to 15 carbon atoms which contains a hetero atom in the carbon skeleton, or an aralkyl group having 7 to 20 carbon atoms which contains a hetero atom in the carbon skeleton; $B^2$ represents a protecting group for the amino group; and X represents a halogen atom, which comprises producing an N-protected α-aminohalomethyl ketone of formula (10):

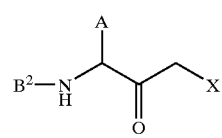

(10)

wherein A, $B^2$, and X are as defined above, and then reducing this ketone, wherein said producing- N-protected α-aminohalomethyl ketone of the following formula (10) comprises:

producing an α-aminohalomethyl ketone of the formula (4):

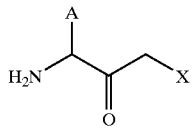
(4)

wherein A and X are as defined above, or a salt thereof, by reacting a 3-oxazolidin-5-one derivative of the following formula (1):

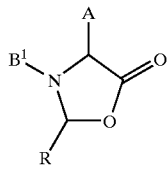
(1)

wherein R represents an unsubstituted or substituted aryl group or lower alkyl group, or a hydrogen atom, $B^1$ represents a protecting group for the amino group, and A is as defined above with a halomethyl lithium to produce a reaction product;

treating the reaction product with an acid; and
then protecting the amino group thereof.

4. A process for producing N-protected β-aminoepoxides of following formula (12):

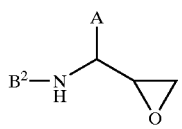
(12)

wherein A represents an unsubstituted or substituted alkyl group having 1 to 10 carbon atoms aryl group having 6 to 15 carbon atoms or aralkyl group, having 7 to 20 carbon atoms, an unsubstituted or substituted alkyl group having 1 to 10 carbon atoms which contains a hetero atom in the carbon skeleton, an aryl group having 6 to 15 carbon atoms which contains a hetero atom in the carbon skeleton, or an aralkyl group having 7 to 20 carbon atoms which contains a hetero atom in the carbon skeleton; and $B^2$ represents a protecting group for the amino group, by which comprises producing an N-protected β-amino alcohol of formula (11) by the process of claim 3, and then treating this alcohol with a base.

5. A process for producing β-aminoalcohols of following formula (13), or a salt thereof:

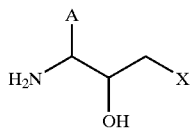
(13)

wherein A represents an unsubstituted or substituted alkyl group having 1 to 10 carbon atoms, aryl group having 6 to 15 carbon atoms or aralkyl group having 7 to 20 carbon atoms, an unsubstituted or substituted alkyl group having 1 to 10 carbon atoms which contains a hetero atom in the carbon skeleton, an aryl group having 6 to 15 carbon atoms which contains a hetero atom in the carbon skeleton, or an aralkyl group having 7 to 20 carbon atoms which contains a hetero atom in the carbon skeleton; and X represents a halogen atom, or salts thereof, by which comprises producing an α-aminohalomethyl ketone of formula (4):

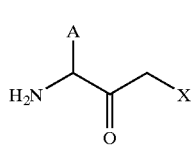
(4)

wherein A and X are as defined above, or a salt thereof, and then reducing this ketone, wherein said producing an α-aminohalomethyl ketone of formula (4) comprises:

reaction a 3-oxazolidin-5-one derivative of the following formula (1):

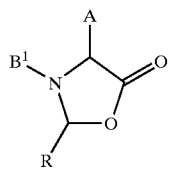
(1)

wherein R represents an unsubstituted or substituted aryl group or lower alkyl group, or a hydrogen atom, and A and $B^1$ are as defined above with a halomethyl lithium to produce a reaction product;

and then treating the reaction product with an acid.

6. A process for producing N-protected β-aminoalcohols of following formula (14):

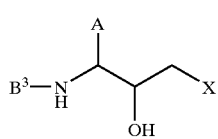
(14)

wherein A represents an unsubstituted or substituted alkyl group having 1 to 10 carbon atoms, aryl group having 6 to 15 carbon atoms or aralkyl group having 7 to 20 carbon atoms, an unsubstituted or substituted alkyl group having 1 to 10 carbon atoms which contains a hetero atom in the carbon skeleton, an aryl group having 6 to 15 carbon atoms which contains a hetero atom in the carbon skeleton, or an aralkyl group having 7 to 20 carbon atoms which contains a hetero atom in the carbon skeleton; $B^3$ represents a protecting group for the amino group; and X represents a halogen atom, which comprises producing a β-aminoalcohol of formula (13) or a salt thereof by the process of claim 5, and then protecting the amino group thereof with a protecting group.

7. A process for producing N-protected β-aminoepoxides of following formula (15):

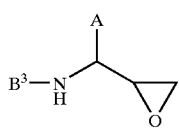

(15)

wherein A represents an unsubstituted or substituted alkyl group having 1 to 10 carbon atoms, aryl group having 6 to 15 carbon atoms or aralkyl group having 7 to 20 carbon atoms, an unsubstituted or substituted alkyl group having 1 to 10 carbon atoms which contains a hetero atom in the carbon skeleton, an aryl group having 6 to 15 carbon atoms which contains a hetero atom in the carbon skeleton, or an aralkyl group having 7 to 20 carbon atoms which contains a hetero atom in the carbon skeleton; and $B^3$ represents a protecting group for the amino group, by which comprises producing an N-protected β-amino alcohol of formula (14) by the process of claim 6, and then treating this alcohol with a base.

* * * * *